United States Patent
Muramatsu et al.

(10) Patent No.: US 6,744,178 B2
(45) Date of Patent: Jun. 1, 2004

(54) PULSE DETECTION DEVICE AND METHOD OF MANUFACTURING THE SAME

(75) Inventors: Hiroyuki Muramatsu, Chiba (JP); Masataka Shinogi, Chiba (JP); Hiroshi Odagiri, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 09/748,326

(22) Filed: Dec. 26, 2000

(65) Prior Publication Data

US 2002/0013534 A1 Jan. 31, 2002

(30) Foreign Application Priority Data

Dec. 27, 1999 (JP) .......................................... 11-370613
Nov. 27, 2000 (JP) ........................................ 2000-359795

(51) Int. Cl.[7] .............................................. H01L 41/08
(52) U.S. Cl. .......................... 310/334; 310/340; 310/344
(58) Field of Search ................................. 310/334–337

(56) References Cited

U.S. PATENT DOCUMENTS

| | | | | | |
|---|---|---|---|---|---|
| 3,859,984 | A | * | 1/1975 | Langley ................. | 128/2.05 Z |
| 4,086,916 | A | * | 5/1978 | Freeman et al. ......... | 128/205 T |
| 4,651,310 | A | * | 3/1987 | Kaneko et al. .......... | 367/140 |
| 5,176,140 | A | * | 1/1993 | Kami et al. ............. | 128/662.03 |
| 6,394,960 | B1 | * | 5/2002 | Shinogi et al. .......... | 600/503 |
| 6,443,900 | B2 | * | 9/2002 | Adachi et al. ........... | 600/458 |

* cited by examiner

Primary Examiner—Mark Budd
(74) Attorney, Agent, or Firm—Adams & Wilks

(57) ABSTRACT

A pulse detection device has a base plate having a first main surface disposable against a part of a living body during use of the pulse detection device, a second main surface disposed opposite the first main surface, and a channel formed in the second main surface. A first piezoelectric element is disposed in the channel of the base plate for transmitting an ultrasonic signal toward an artery in the living body. A second piezoelectric element is disposed in the channel of the base plate for receiving the ultrasonic signal transmitted by the first piezoelectric element and reflected by the artery.

21 Claims, 9 Drawing Sheets

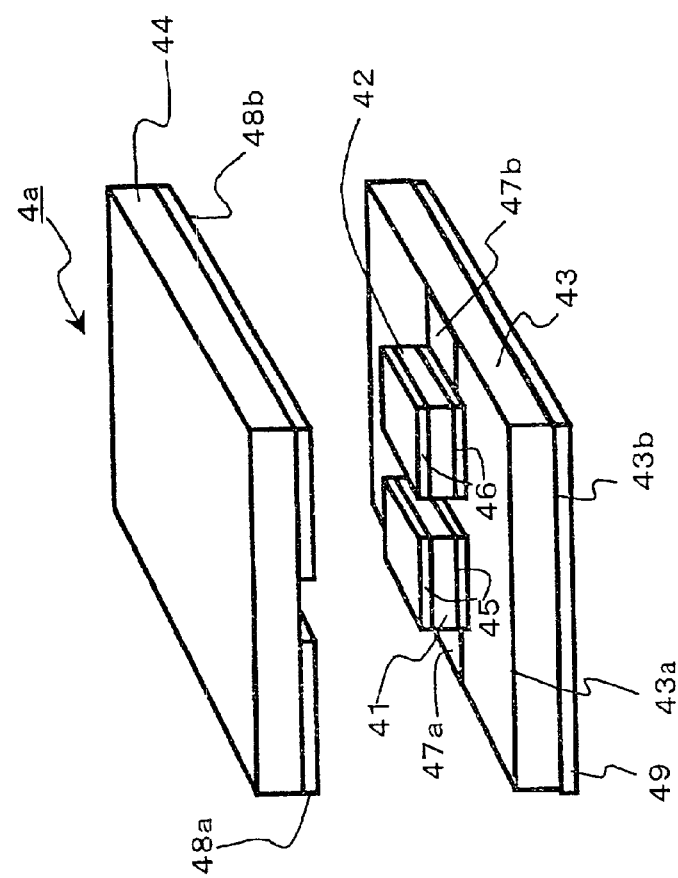
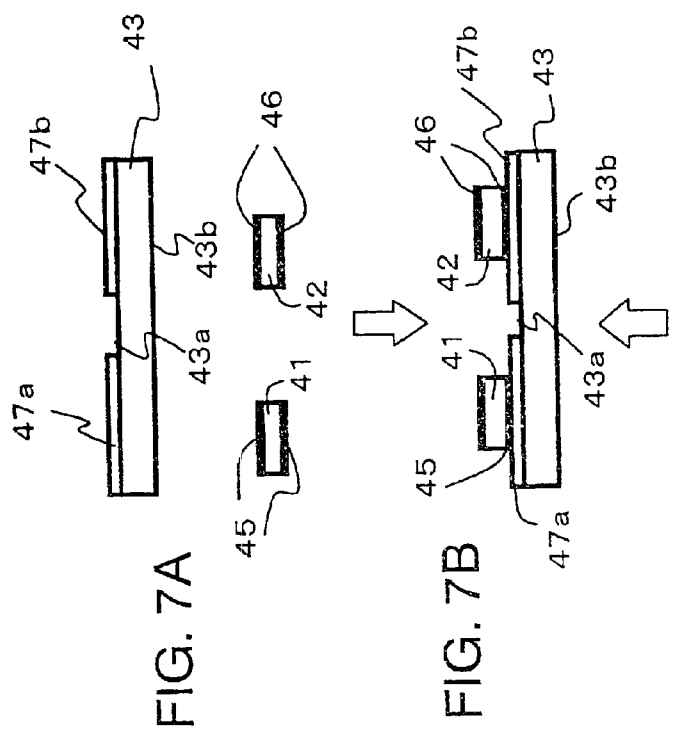
FIG. 7A
FIG. 7B
FIG. 8

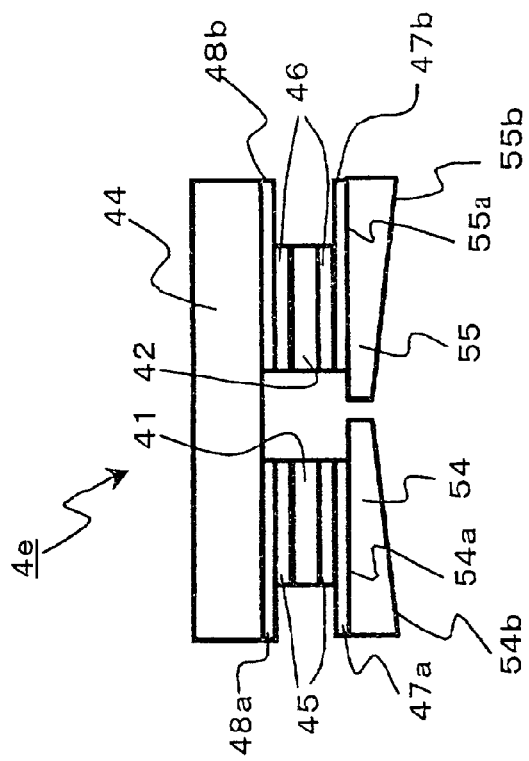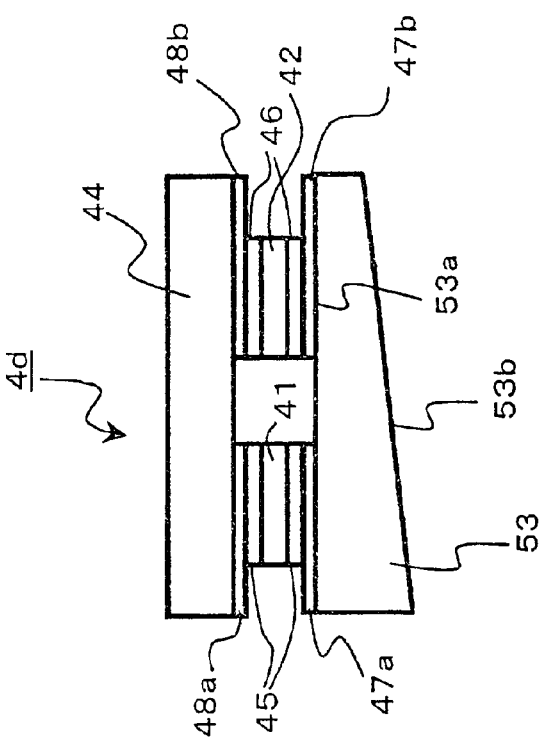

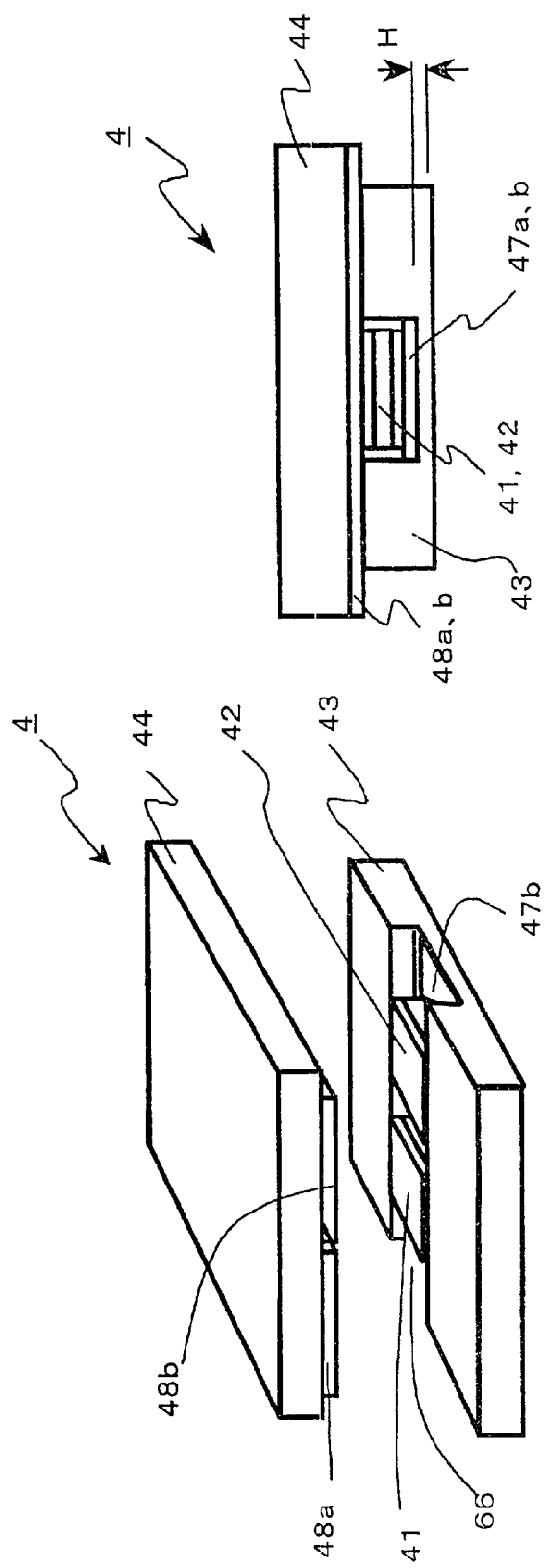

PULSE DETECTION DEVICE AND METHOD OF MANUFACTURING THE SAME

BACKGROUND OF THE INVENTION

1. Field of the Invention

The present invention relates to a pulse detection device using a piezoelectric element and a method of manufacturing the pulse detection device.

2. Description of the Related Art

A pulse in a living body contains important information for diagnosis of a sickness. In recent years, studies have been conducted on application of a system in which a portable pulse detection device is worn about an arm of a patient at a medical office of a medical institution, e.g., a hospital, and data on a pulse detected from the patient, which is transmitted from the portable pulse detection device, is received on the hospital side to grasp the condition of the patient. Use of a piezoelectric element in a pulse detection device is advantageous in terms of the effect of reducing the device in size and in weight. The development of pulse detection devices, including those suitably applicable to the above-described system, is being advanced.

FIGS. 19 and 20 show a conventional pulse detecting device 100 using a piezoelectric element. As shown in FIG. 19, the pulse detection device 100 has two piezoelectric elements 110 and 120 fixed by being embedded in a resin 130 (or gel). FIG. 20 is a side view of the pulse detection device 100 shown in FIG. 20. The piezoelectric elements 110 and 120 are fixed while being spaced apart by a distance g. Further, the fixing step is controlled such that the thickness t between the piezoelectric elements 110 and 120 and a surface 150 to be brought into contact with a skin is set to a predetermined value.

In each of the piezoelectric elements 110 and 120, metal electrodes (not shown) are formed on two surfaces opposite from each other in the direction of thickness. Probes (terminals, leads, or the like) (not shown) for application of a drive voltage are connected to both the electrodes of the piezoelectric element 110 while probes (not shown) for outputting a voltage signal are connected to the upper and lower electrodes of the piezoelectric element 120.

This pulse detection device 110 is used to detect a pulse of a patient at the time of medical examination in a hospital. More specifically, when a drive voltage is applied to both the electrodes of the piezoelectric element 110, the piezoelectric element 110 is excited to generate ultrasound, which is transmitted into the living body through the resin 130. The ultrasound transmitted into the living body is reflected by a bloodstream in the living body. The reflected ultrasound is received by the piezoelectric element 120 through the resin 130.

At this time, a difference is caused between the frequency of the ultrasound transmitted by the piezoelectric element 110 and the frequency of the ultrasound received by the piezoelectric element 120 by the Doppler effect of the bloodstream. Since the speed of the bloodstream changes in synchronization with pulsation, a pulse in the living body is detected from changes in the frequency of the ultrasound.

In the above-described pulse detection device using the piezoelectric elements, there is a need to precisely place the ultrasound transmitting piezoelectric element 110 and the ultrasound receiving piezoelectric element 120 for the purpose of improving the ultrasound receiving sensitivity. The pulse detection sensitivity changes largely with respect to the spacing g between the two piezoelectric elements 110 and 120. An optimum range of this spacing is from 0.1 to 0.5 mm. The sensitivity also changes largely with respect to the thickness t of the block of the resin 130. For example, if the piezoelectric elements 110 and 120 are driven at 9.0 MHz, an optimum value of the thickness t is about 140 $\mu$m.

However, it is difficult to precisely place the piezoelectric elements 110 and 120 of the above-described pulse detection device 100, because the manufacturing process of the pulse detection device 100 uses the step of pouring the resin 130 after placing the two piezoelectric elements 110 and 120 at predetermined positions and there is a possibility of occurrence of changes in the positions and the angles of the placed piezoelectric elements when the resin is poured.

Therefore, there is a possibility of the conventional pulse detection devices 100 being manufactured with considerable variation in quality. In the step of forming the piezoelectric element by pouring the resin 130, it is difficult to control the thickness h of the resin 130 in accordance with the desired thickness, so that there is a possibility of occurrence of considerable variation in sensitivity.

Further, because of the need to apply a voltage between the two surfaces opposite in the thickness direction of each of the piezoelectric elements 110 and 120 embedded in the resin 130, the step of attaching thin wires or the like to the two surfaces of the piezoelectric elements 110 and 120 is required before the step of pouring the resin 130. Therefore, it is difficult to suitably place the piezoelectric elements 110 and 120, and the number of steps is increased. Thus, it is difficult to manufacture the pulse detection device.

SUMMARY OF THE INVENTION

In view of the above-described problems, an object of the present invention is to provide a pulse detection device in which an ultrasound transmitting piezoelectric element and an ultrasound receiving piezoelectric element are precisely placed to effectively limit variation in quality, and a method of manufacturing the pulse detection device.

Another object of the present invention is to provide a pulse detection device which is formed by using a base plate having a prescribed thickness to have an optimum pulse detection sensitivity, instead of resin, and which can be manufactured with improved reproducibility.

Still another object of the present invention is to provide a pulse detection device in which wiring for application of a voltage to piezoelectric elements is provided on a supporting base plate to easily manufacture the pulse detection device.

A further object of the present invention is to provide a pulse detection device having an improved pulse detection sensitivity.

To achieve the above-described objects, according to an aspect of the present invention, there is provided a pulse detection device comprising a transmitting piezoelectric element (e.g., transmitting piezoelectric element 41 shown in FIG. 4) excited in accordance with a drive signal to generate ultrasound and to transmit the ultrasound into a living body, a receiving piezoelectric element (e.g., receiving piezoelectric element 42 shown in FIG. 4) for receiving reflected waves of the ultrasound transmitted into the living body and reflected by a bloodstream in the living body, and for converting the reflected waves into an electrical signal, a detection section (e.g., processing computation section 31 shown in FIG. 3) for detecting a pulse from the ultrasound generated by the transmitting piezoelectric element and the reflected waves received by the receiving piezoelectric element, and a transmitting/receiving base plate (e.g., transmitting/receiving base plate 43) having the transmitting piezoelectric element and the receiving piezoelectric element placed and fixed on its one surface, the other surface of the transmitting/receiving base plate being brought into contact with the living body.

In the thus-constructed pulse detection device, both the transmitting piezoelectric element and the receiving piezoelectric element are placed and fixed on the transmitting/receiving base plate. Therefore, these piezoelectric elements can be placed with accuracy in accordance with a design.

There is no functional problem since the ultrasound generated by the transmitting piezoelectric element is transmitted into the living body through the transmitting/receiving base plate, and the waves reflected by the bloodstream in the living body propagate from the living body to the receiving piezoelectric element through the transmitting/receiving base plate.

According to the present invention, therefore, it is possible to provide a pulse detection device with a reduced possibility of occurrence of variation in quality. It is also possible to improve the pulse detection sensitivity of the pulse detection device.

The acoustic impedance of the transmitting/receiving base plate is set to an intermediate value between the acoustic impedance of each of the piezoelectric elements and the acoustic impedance of the living body.

The acoustic impedance of the transmitting/receiving base plate is set to an intermediate value between the acoustic impedance of each of the piezoelectric elements and the acoustic impedance of the living body to enable the ultrasound generated by the transmitting piezoelectric element to be efficiently transmitted into the living body without being reflected at the interface between the transmitting/receiving base plate and the living body. Further, it is possible to receive the reflected waves by the pule in the living body with the receiving piezoelectric element with high sensitivity without being reflected at the interface.

A glass base plate having a thickness of about ¼ of the wavelength of the ultrasound generated by the transmitting piezoelectric element may be used as the transmitting/receiving base plate. The amount of reflection of the ultrasound at the interface between the glass base plate and the living body can be reduced by using such a glass base plate, thereby enabling efficient transmission of the ultrasound into the living body and enabling the receiving piezoelectric element to receive the reflected waves with high sensitivity.

Further, a resin layer (e.g., resin layer 49 shown in FIG. 8) may be provided on the other surface of the transmitting/receiving base plate. The material of the resin layer may be selected to optimize, according to use of the pulse detection device, the characteristics of the surface to be brought into contact with the living body.

For example, an epoxy-based resin is used to form the resin layer. Since the acoustic impedance of the epoxy-based resin is an intermediate value between the acoustic impedance of the transmitting/receiving base plate and the acoustic impedance of the living body, the amount of reflection of the ultrasound at the interface between the transmitting/receiving base plate and the living body can be further reduced by using the epoxy-based resin layer, thereby enabling efficient propagation of the ultrasound.

If a silicone-based resin, for example, is used to form the resin layer, the closeness of contact between the transmitting/receiving base plate and the living body can be improved. Correspondingly, the amount of intrusion of air at the interface between the transmitting/receiving base plate and the living body is reduced and the attenuation of the ultrasound is thereby reduced. As a result, the efficiency of propagation of the ultrasound is improved. The silicone-based resin is favorable in terms of compatibility with the living body and can be used by being maintained in intimate contact with the skin of the living body without any considerable risk of affecting the skin.

The above-described pulse detection device may constructed in such a manner that a groove (groove 50*a* shown in FIG. 9) is formed in a portion of the transmitting/receiving base plate, and the transmitting piezoelectric element and the receiving piezoelectric element are placed on the transmitting/receiving base plate on the opposite sides of the groove.

According to this arrangement, the ultrasound generated by the transmitting piezoelectric element is reflected and attenuated at the groove between the transmitting piezoelectric element and the receiving piezoelectric element on the transmitting/receiving base plate. Thus, the possibility of the ultrasound propagating through the transmitting/receiving base plate to be directly received by the receiving piezoelectric element is reduced. Consequently, noise can be reduced and the reliability of the pulse detection device can be improved.

Alternatively, the transmitting/receiving base plate may be divided into two. The transmitting piezoelectric element may be placed on one of the divided transmitting/receiving base plates (e.g., transmitting/receiving base plate 51 shown in FIG. 10), and the receiving piezoelectric element may be placed on the other divided transmitting/receiving base plate (e.g., transmitting/receiving base plate 52 shown in FIG. 10). In such a case, the ultrasound generated by the transmitting piezoelectric element does not propagate directly to the receiving piezoelectric element. Thus, noise can be reduced and the reliability of the pulse detection device can be improved.

The other surface of the transmitting/receiving base plate (e.g., transmitting/receiving base plate 53 shown in FIG. 11) may be formed so as to be slanted relative to the surface on which the piezoelectric elements are placed. For example, the two surfaces of the transmitting/receiving base plate are formed so as to be not parallel but tapered, thereby enhancing the Doppler effect of the bloodstream in the living body to increase the difference between the frequency of the ultrasound generated by the transmitting piezoelectric element and the reflected waves received by the receiving piezoelectric element. Consequently, the pulse detection sensitivity of the pulse detection device is improved.

A supporting base plate (e.g., supporting base plate 44 shown in FIG. 4) for supporting the transmitting piezoelectric element and the receiving piezoelectric element positioned on the transmitting/receiving base plate may be provided.

If such a supporting base plate is provided, the strength of the pulse detection device against an impact externally applied can be improved, thereby improving the durability of the device.

Further, the supporting base plate 44 provided in the pulse detection device is effective in preventing leakage of ultrasound.

A display section may be provided to display a pulse detected by the detection section.

A belt (e.g., band 5 shown in FIG. 1) for enabling the pulse detection device to be worn about a wrist may be provided to enable the living body to easily carry the pulse detection device.

The transmitting piezoelectric element and/or the receiving piezoelectric element, and the transmitting/receiving base plate may be joined to each other by intermetallic bonding.

Intermetallic bonding is a method of joining two metals by maintaining the two metals in contact with each other, and pressing and heating the metals to cause thermal diffusion of metal atoms between the metals.

In the thus-constructed pulse detection device, the transmitting/receiving base plate and each of the transmitting piezoelectric element and the receiving piezoelectric element are joined by intermetallic bonding. The attenuation of ultrasound at the joint surface in the case of joining by intermetallic bonding is smaller than that in the case of joining by using an adhesive. Thus, efficient propagation of ultrasound can be achieved.

A sealing material such as a silicone resin may be provided between the transmitting/receiving base plate and the supporting base plate. In the thus-arranged pulse detection device, it is possible to prevent sweat or the like from attaching to the transmitting piezoelectric element and the receiving piezoelectric element during use and, hence, to prevent a reduction in sensitivity. The sealing material is provided such that a gap is set between the sealing material and each of the transmitting piezoelectric element and the receiving piezoelectric element, so that external vibration cannot easily propagate to the piezoelectric elements through the sealing material. Thus, it is possible to prevent sweat or the like from entering the pulse detection device and to further improve the effect of preventing a reduction in sensitivity.

The pulse detection device may also be constructed in such a manner that a channel is formed in the transmitting/receiving base plate and the piezoelectric elements are placed in the channel, thereby enabling the transmitting/receiving base plate and the supporting base plate to be fixed to each other in addition to a joining surface between the transmitting and receiving piezoelectric elements and the transiting/receiving base plate and a joining surface between the transmitting and receiving piezoelectric elements and the supporting base plate. Thus, durability of the device can be improved. Further, the thickness of the portion of the transmitting/receiving base plate remaining after the formation of the channel is set to an optimum value to enable efficient transmission and reception of ultrasound without changing the thickness of the entire transmitting/receiving base plate.

Feeding portions (transmitting/receiving base plate electrodes) to which an electrical signal is applied may be provided on one surface of the transmitting/receiving base plate on which the piezoelectric elements are placed, and feeding portions (supporting base plate electrodes) to be electrically connected to the transmitting/receiving base plate electrodes may be provided on the surface of the supporting base plate on which the piezoelectric elements are supported. The transmitting/receiving base plate electrodes and the supporting base plate electrodes are electrically connected to each other. In this manner, the amount of wiring for application of electrical signals to the transmitting piezoelectric element and the receiving piezoelectric element can be reduced.

According to another aspect of the present invention, there is provided a method of manufacturing a pulse detection device comprising the steps of forming wiring metal films on a transmitting/receiving base plate, and an electrode metal film on a transmitting piezoelectric element and on a receiving piezoelectric element, placing the transmitting piezoelectric element and the receiving piezoelectric element on the transmitting/receiving base plate such that the metal films are laid on each other, and joining the transmitting piezoelectric element and the receiving piezoelectric element to the transmitting/receiving base plate by using intermetallic bonding between the metal films to fix the transmitting piezoelectric element and the receiving piezoelectric element on the transmitting/receiving base plate and to establish an electrical connection between the transmitting/receiving base plate and each of the transmitting piezoelectric element and the receiving piezoelectric element.

BRIEF DESCRIPTION OF THE DRAWINGS

In the accompanying drawings:

FIGS. 7A and 7B are diagrams showing steps in a method of manufacturing the measuring unit according to the present invention: FIG. 7A is a diagram showing a step of forming electrodes; and FIG. 7B is a diagram showing a step of joining piezoelectric elements to a surface of a transmitting/receiving base plate;

FIG. 8 is a diagram showing the structure of a measuring unit in which a resin layer is provided on the other surface of the transmitting/receiving base plate;

FIG. 11 is a diagram showing the structure of a measuring unit having a tapered transmitting/receiving base plate;

FIG. 12 is a diagram showing a measuring unit having divided transmitting/receiving base plates each having a tapered shape;

FIG. 15 is a diagram showing a structure in which a channel is formed in a transmitting/receiving base plate, and a transmitting piezoelectric element and a receiving piezoelectric element are placed in the channel;

FIG. 16 is a side view of the structure shown in FIG. 15;

DETAILED DESCRIPTION OF THE PREFERRED EMBODIMENTS

In a pulse detection device according to the present invention, a piezoelectric element for transmitting ultrasound into a living body in accordance with a drive signal, or receiving reflected waves of ultrasound reflected by a bloodstream in a living body is provided on a surface of a base plate, and the other surface of the base plate opposite from the surface on which the piezoelectric element is provided is brought into contact with the living body. In the thus-constructed device, the piezoelectric element is placed and fixed on the base plate. Therefore, the piezoelectric element can be placed with accuracy as specified in a design. Consequently, it is possible to reduce variation in the quality of the pulse detection device and to improve the pulse detection sensitivity.

The piezoelectric element and the base plate are joined to each other by intermetallic bonding between electrodes respectively formed on the surfaces of the piezoelectric element and the base plate. The acoustic impedance of the base plate is set to an intermediate value between the acoustic impedance of the piezoelectric element and the acoustic impedance of the living body. The thickness of the base plate is set to about ¼ of the wavelength of ultrasound generated by the piezoelectric element. A resin layer is formed on the surface of the base plate opposite from the surface on which the piezoelectric element is provided. A supporting base plate for supporting the piezoelectric element mounted on the base plate is also provided. The piezoelectric element is sandwiched between the base plate and the supporting base plate. Details of the pulse detection device are as described below.

A pulse detection device and a method of manufacturing the pulse detection device according to the present invention will be described with reference to the accompanying drawings.

A pulse detection device 1 will first be described with respect to its external views shown in FIGS. 1 and 2.

Figure 2:
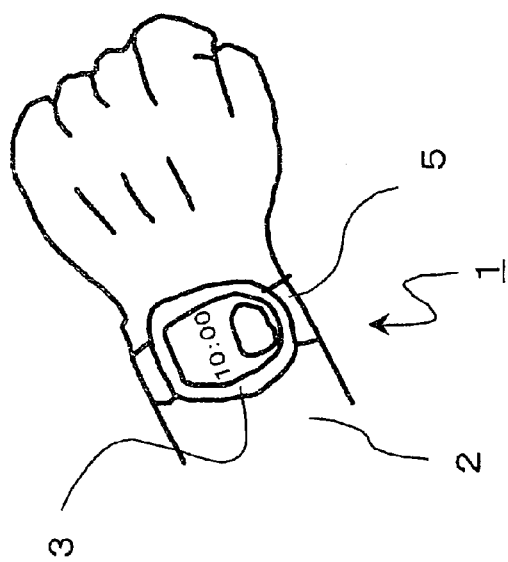
FIG. 2 is a view of an external appearance of the pulse detection device of the present invention in a state where the device is fitted around a part of a living body (wrist)
Figure 1:
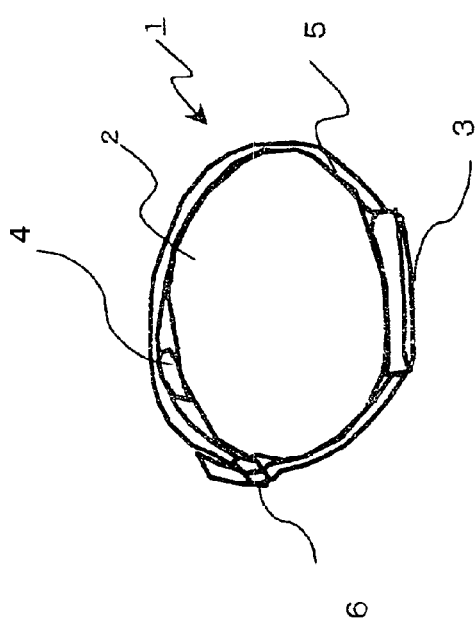
FIG. 1 is a view of the external configuration of a pulse detection device to which the present invention is applied.

FIG. 1 is a side view of the external configuration of the pulse detection device 1, and FIG. 2 is an illustration showing a state where the pulse detection device 1 shown in FIG. 1 is fitted around a part of living body 2 (wrist).

As shown in FIG. 1, the pulse detection device 1 is mainly constituted of a processing unit 3, a measuring unit 4, a band 5, and a metal clasp 6. The pulse detection device 1 is carried at all times by being fitted around the living body part 2, as shown in FIG. 2. The processing unit 3 and the measuring unit 4 are attached to the band 5 and are supported on the living body 2 (indicated by the broken line in the figure) by the band 5 and the metal clasp 6. In this state, the measuring unit 4 is brought into contact with the living body 2 in the vicinity of the radial artery or the ulnar artery (not shown). Although not shown in the figure, the processing unit 3 and the measuring unit 4 are connected to each other by leads, and a drive voltage signal is supplied from the processing unit 3 to the measuring unit 4 via the leads and a voltage signal obtained as a measurement result is supplied from the measuring unit 4 to the processing unit 3 via the leads.

Figure 3:
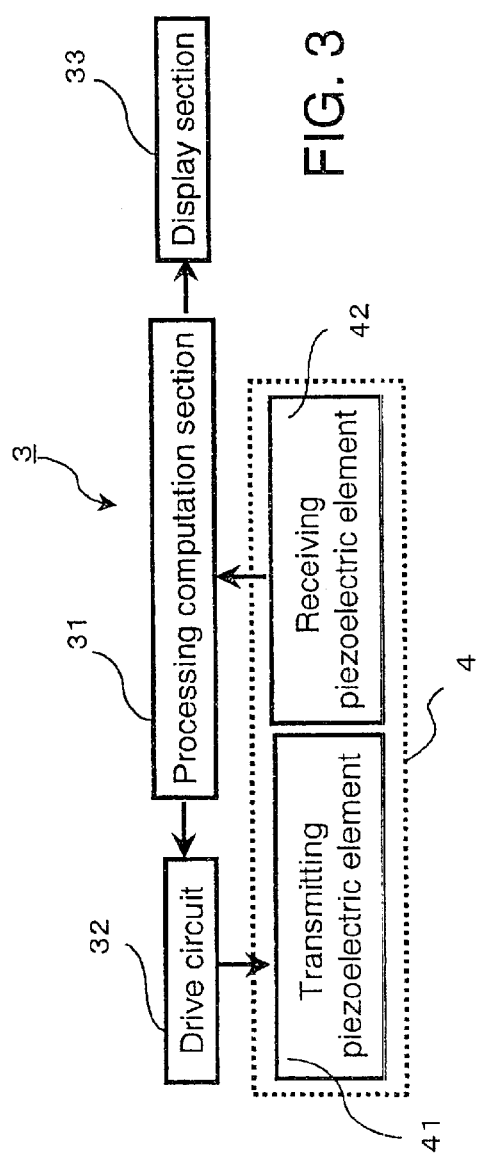
FIG. 3 is a block diagram showing the internal configuration of a processing unit and a state of connection to a measuring unit.

The processing unit 3 of the pulse detection device 1 will be described with reference to FIG. 3. FIG. 3 is a block diagram showing the internal configuration of the processing unit 3 and the state of connection between the processing unit 3 and the measuring unit 4. As shown in FIG. 3, the processing unit 3 is mainly constituted of a processing computation section 31, a drive circuit 32, and a display section 33.

The processing computation section 31 executes a processing program stored in an internal memory area (not shown) to perform various kinds of processing relating to detection of a pulse, and displays processing results on the display section 33.

The processing computation section 31 makes the drive circuit 32 output a particular drive voltage signal to a transmitting piezoelectric element 41 (described below in detail) provided in the measuring unit 4.

The processing computation section 31 detects a pulse by comparing the frequency of ultrasound transmitted from the transmitting piezoelectric element 41 and the frequency of ultrasound received by a receiving piezoelectric element 42, which has been changed according to the Doppler effect of a bloodstream.

The drive circuit 32 outputs a particular drive voltage signal to the transmitting piezoelectric element 41 of the measuring unit 4 in accordance with an instruction from the processing computation section 31.

The display section 33 is constituted of a liquid crystal display screen and the like, and displays a pulse detection result supplied from the processing computation section 31, and other kinds of information.

Figure 4:
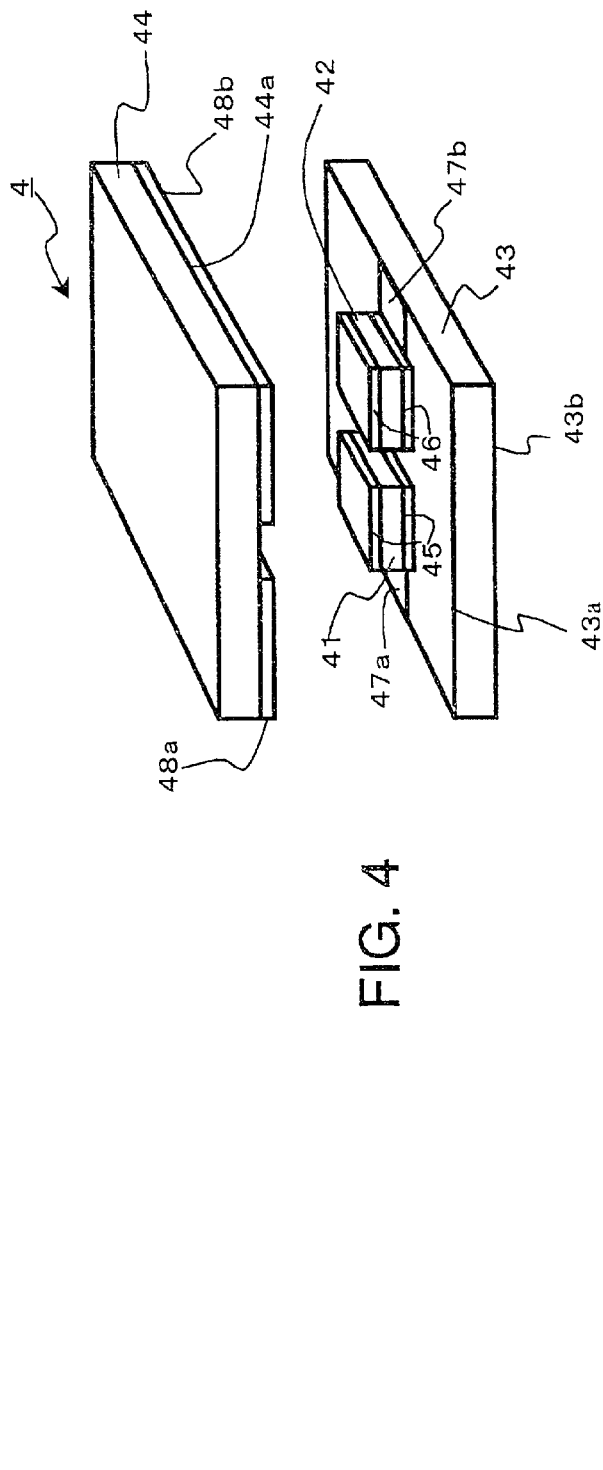
FIG. 4 is a diagram showing the construction of the measuring unit of the pulse detection device according to the present invention.

The measuring unit 4 of the pulse detection device 1 will next be described with reference to FIGS. 4 and 5. FIG. 4 is a diagram schematically showing the construction of the measuring unit 4, and FIG. 5 is a schematic cross-sectional view of the structure of the measuring unit 4.

As shown in FIG. 4, the measuring unit 4 is mainly constituted of the transmitting piezoelectric element 41, the receiving piezoelectric element 42, a transmitting/receiving base plate 43, and a supporting base plate 44.

The transmitting piezoelectric element 41 and the receiving piezoelectric element 42 have a pair of electrodes 45 and a pair of electrodes 46, respectively. Each pair of electrodes 45 and 46 are formed on both the surfaces of the piezoelectric element 41 or 42 in the direction of thickness. Electrodes 47a and 47b are formed on a surface 43a of the transmitting/receiving base plate 43. Electrodes 48a and 48b are formed on a surface 44a of the supporting base plate 44. The electrodes 45, 46, 47a, 47b, 48a, and 48b are films of a metal, e.g., Au or Pt, and are formed by vapor deposition or the like.

Figure 5:
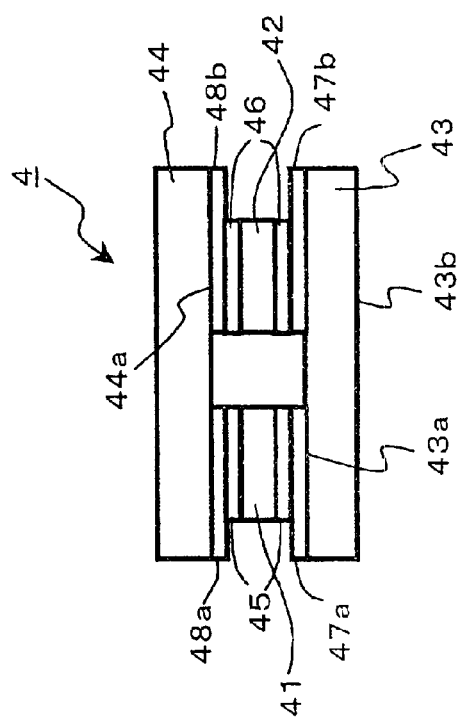
FIG. 5 is a schematic sectional view of the structure of the measuring unit.

As shown in FIG. 5, the transmitting piezoelectric element 41 is placed and fixed on the surface 43a of the transmitting/receiving base plate 43 with its electrode 45 and the electrode 47a laid on each other, and the receiving piezoelectric element 42 is placed and fixed on the transmitting/receiving base plate 43 with its electrode 46 and the electrode 47b laid on each other. Further, in order to hold the two piezoelectric elements 41 and 42, the supporting base plate 44 is placed and fixed on the piezoelectric elements 41 and 42 with its electrode 48a and the electrode 45 of the transmitting piezoelectric element 41 laid on each other, and with its electrode 48b and the electrode 46 of the receiving piezoelectric element 42 laid on each other. These combinations of the electrodes laid on each other are electrically connected.

Two piezoelectric elements identical to each other may be used as the transmitting piezoelectric element 41 and the receiving piezoelectric element 42. The shape of the piezoelectric elements 41 and 42 may be freely selected and piezoelectric elements differing in shape from each other may be respectively used for transmitting and receiving.

The measuring unit shown in FIGS. 4 and 5 is manufactured by a process described below.

The two electrodes 45 of the transmitting piezoelectric element 41 are connected to the drive circuit 32 of the processing unit 3 by the leads. When the drive circuit 32 applies a particular drive voltage signal to the two electrodes 45 of the transmitting piezoelectric element 41, the transmitting piezoelectric element 41 is excited to generate ultrasound of a particular frequency, which is transmitted into a living body (indicated at 2 in FIG. 6).

The two electrodes 46 of the receiving piezoelectric element 42 are connected to the processing computation section 31 of the processing unit 3 by the leads. When the receiving piezoelectric element 42 receives ultrasound from a living body, it converts the ultrasound into a voltage signal and outputs this signal to the processing computation section 31 of the processing unit 3.

The transmitting/receiving base plate 43 is, for example, a glass base plate in which the transmitting piezoelectric element 41 and the receiving piezoelectric element 42 are placed on the surface 43a, and the other surface 43b is brought into contact with a living body.

To enable efficient propagation of ultrasound between each of the piezoelectric elements 41 and 42 and a living body through the transmitting/receiving base plate 43, it is necessary to set the acoustic impedance of the transmitting/receiving base plate 43 to a value between the acoustic impedance Zl of the living body and the acoustic impedance Zc of the piezoelectric element. The acoustic impedance is a value that indicates the facility with which an acoustic wave propagates. The value of the acoustic impedance changes with respect to the Young's modulus and the density of the medium.

The ideal acoustic impedance Zm of the transmitting/receiving base plate 43 in the measuring unit 4 constructed as shown in FIG. 5 is expressed by $$Zm = (Zc \times Zl)^{1/2} \quad (1)$$

Zl=1.5 M (N·sec/m$^3$) and Zc (when PZT is used)=30 M (N·sec/m$^3$), which are known values, are substituted in the equation (1) to obtain Zm=about 6.7 M (N·sec/m$^3$).

In this embodiment, by considering this computed value, a glass base plate having an acoustic impedance of about 10 M (N·sec/m$^3$) is used as the transmitting/receiving base plate 43.

In factors relating to propagation of ultrasound, the thickness of the transmitting/receiving base plate 43 is also important. If the thickness of the transmitting/receiving base plate 43 is inappropriate, reflection of ultrasound is caused at the transmitting/receiving base plate 43 to reduce the efficiency of propagation of ultrasound, as is an undesirable condition of the above-described acoustic impedance. Preferably, the thickness of the transmitting/receiving base plate 43 is set to about ¼ of the wavelength at the frequency of ultrasound transmitted through the transmitting/receiving base plate 43. More specifically, if the frequency of ultrasound is 9 MHz (ultrasound of 2.3 to 10 MHz being ordinarily used), and if the speed of sound in the transmitting/receiving base plate (glass plate) 43 is about 5000 m/s, the thickness of the transmitting/receiving base plate 43 is set to about 140 µm.

The operation of the processing unit 3 and the measuring unit 4 in the pulse detection device 1 will now be described with reference to FIGS. 3 and 6.

Figure 6:
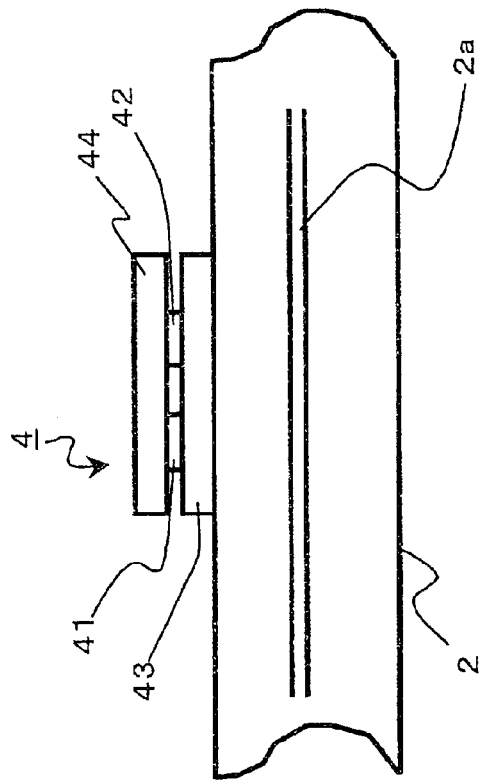
FIG. 6 is a diagram showing a state where the measuring unit is brought into contact with a living body.

First, when the pulse detection device 1 is fitted on the living body 2, the measuring unit 4 is brought into contact with the living body 2 (in the vicinity of the radial artery or the ulnar artery), as shown in FIG. 6. To detect a pulse, the processing computation circuit 31 shown in FIG. 3 makes the drive circuit 32 output a particular drive voltage signal to the electrodes 45 (see FIG. 5) of the transmitting piezoelectric element 41.

The transmitting piezoelectric element 41 is excited on the basis of the inputted drive voltage signal to generate ultrasound and to transmit the ultrasound into the living body 2 (see FIG. 6) through the transmitting/receiving base plate 43. The ultrasound transmitted into the living body 2 is reflected by a bloodstream 2a, and the ultrasound reflected by the bloodstream 2a is received by the receiving piezoelectric element 42 of the measuring unit 4. The receiving piezoelectric element 42 converts the received ultrasound into a voltage signal and outputs the signal to the processing computation section 31 through the two electrodes 46 (see FIG. 5).

The processing computation section 31 detects a pulse in the living body by comparing the frequency of the ultrasound transmitted from the transmitting piezoelectric element 41 and the frequency of the ultrasound received by the receiving piezoelectric element 42, which has been changed according to the Doppler effect of the bloodstream. The processing computation section 31 displays a pulse detection result on the display section 33. Thus, the pulse detection device 1 measures and displays a pulse in the living body.

A method of manufacturing the measuring unit 4 of the pulse detection device having piezoelectric elements formed on the transmitting/receiving base plate will next be described with reference to FIGS. 7A and 7B. FIG. 7A is a diagram showing a step of forming electrodes, and FIG. 7B is a diagram showing a step of bonding piezoelectric elements 41 and 42 to a surface 43a of a transmitting/receiving base plate 43.

First, as shown in FIG. 7A, electrodes 45 are formed on two surfaces of the transmitting piezoelectric element 41 opposite from each other in the direction of thickness, and electrodes 46 are formed on two surfaces of the transmitting piezoelectric element 42 opposite from each other in the direction of thickness. Further, two electrodes 47a and 47b are formed on the surface 43a of the transmitting/receiving base plate 43. The electrodes 45, 46, 47a, and 47b are films of a metal, e.g., Au or Pt, and are formed by vapor deposition or the like.

While in the above-described step the electrodes are formed on each of the piezoelectric elements 41 and 42, alternatively a piezoelectric element having electrodes formed thereon may be divided into piezoelectric elements 41 and 42 with electrodes.

Next, as shown in FIG. 7B, the transmitting piezoelectric element 41 is placed on the surface 43a of the transmitting/receiving base plate 43 with its electrode 45 and the electrode 47a of the transmitting/receiving base plate 43 laid on each other. Further, the receiving piezoelectric element 42 is placed on the surface 43a of the transmitting/receiving base plate 43 with its electrode 46 and the electrode 47b of the transmitting/receiving base plate 43 laid on each other.

The piezoelectric elements 41 and 42 and the transmitting/receiving base plate 43 are pressed against each other by being pressed from above and below (indicated by arrows in FIG. 7B) by a press (not shown) or the like and heated with a heater (not shown) or the like.

Heating and pressing performed in this manner cause thermal diffusion of metal atoms between the electrode 45 and the electrode 47a and between the electrode 46 and the electrode 47b, thereby bonding the electrodes (intermetallic bonding). Thus, the piezoelectric elements 41 and 42 are bonded to the surface 43a of the transmitting/receiving base plate 43.

In this embodiment, the transmitting piezoelectric element 41 and the receiving piezoelectric element 42 are placed on the transmitting/receiving substrate 43 in the above-described manner. Therefore, the transmitting piezoelectric element 41 and the receiving piezoelectric element 42 can be placed on the transmitting/receiving substrate 43 with accuracy. Consequently, the pulse detection device 1 having the measuring unit 4 uniform in quality and free from any considerable variation in quality can be provided. Further, the pulse detection device 1 can have improved pulse detection sensitivity.

The piezoelectric elements are not embedded in a resin to be fixed as in the prior art. According to the manufacturing method of the present invention, electrodes can be easily formed on both the surfaces of each of the transmitting piezoelectric element 41 and the receiving piezoelectric element 42, and leads can be easily extended from each of the piezoelectric elements 41 and 42.

Further, the supporting base plate 44 is provided in the pulse detection device 1 to increase the strength of the pulse detection device 1, thereby improving the durability of the pulse detection device 1. Because electrical connections between the supporting base plate 44 and the piezoelectric elements 41 and 42 can be established simultaneously with the fixation, connections of the electrodes of the piezoelectric elements 41 and 42 to leads can be further facilitated.

The supporting base plate 44 provided in the pulse detection device 1 is effective in preventing leakage of ultrasound.

Since intermetallic bonding is used to join the transmitting piezoelectric element 41 and the receiving piezoelectric element 42 to transmitting/receiving substrate 43, no bonding layer is formed at the joint interface. Thus, the attenuation of ultrasound vibration at the joint interface can be reduced.

The pulse detection device 1 of the present invention ordinarily measures and displays pulsation. However, it is also possible to measure pulse waves.

The present invention is not limited to this embodiment with respect to its details described above as contents of the embodiment, and various changes and modifications of this embodiment can be made without departing from the scope of the present invention. For example, the transmitting piezoelectric element 41 and the receiving piezoelectric element 42, joined to the transmitting/receiving base plate 43 by intermetallic bonding in this embodiment, may alternatively be joined to the transmitting/receiving base plate 43 by hydrogen bonding. Joining of these members based on hydrogen bonding is performed in such a manner that water is ionized by using an ion source, hydroxide ions OH⁻ are then produced and applied to the surface of the transmitting/receiving base plate 43, and the transmitting/receiving base plate 43 and the piezoelectric elements 41 and 42 are thereafter press-bonded to each other. Further, a hydrophilic group may be formed on the transmitting/receiving base plate 43, and the transmitting/receiving base plate 43 and the piezoelectric elements 41 and 42 may be joined by hydrogen bonding using the hydrophilic group. The method of joining the transmitting/receiving base plate 43 and the piezoelectric elements 41 and 42 by hydrogen bonding as described above has the advantage of reducing the attenuation of ultrasound vibration at the joint interface in comparison with the case of joining using an adhesive.

In this embodiment, the processing unit 3 and the measuring unit 4 are constructed separately from each other. Alternatively, the processing unit 3 and the measuring unit 4 may be combined into one module. If the processing unit 3 and the measuring unit 4 are formed as one module, the number of components of the pulse detection device 1 is reduced, the manufacturing cost can be limited, and simpler wiring or a smaller amount of wiring may suffice for the connection between the processing unit 3 and the measuring unit 4.

A section for wireless communication or the like may be provided in the processing unit 3 to transmit pulse measurement results to a control system in a hospital. Through such a communication system, the condition of a patient carrying the pulse detection device 1 can be grasped at all times.

Modifications of the construction of the measuring unit 4 shown in FIG. 4 will be described with reference to FIGS. 8 through 18. In FIGS. 8 through 18, the same portions or components as those of the measuring unit 4 shown in FIG. 4 are indicated by the same reference characters. The description thereof will not be repeated.

FIG. 8 shows the construction of a measuring unit 4a in which a resin layer 49 is formed on the other surface 43b of the transmitting/receiving base plate 43. As shown in FIG. 8, the resin layer 49 is formed on the other surface 43b of the transmitting/receiving base plate 43.

The resin layer 49 is formed of an epoxy-based resin or a silicone-based resin. The surface of the transmitting/receiving base plate 43 (the other surface 43b) to be brought into contact with a living body is changed in characteristics in accordance with the kind of resin used to form this layer.

For example, if an epoxy-based resin is used to form the resin layer 49, the amount of reflection of ultrasound caused at the interface between the living body and the transmitting/receiving base plate 43 can be further reduced. This is because the epoxy-based resin has an intermediate acoustic impedance between the acoustic impedance of the transmitting/receiving base plate 43 and the acoustic impedance of the living body. Consequently, it is possible to improve the efficiency of propagation of ultrasound between the living body and the transmitting/receiving base plate 43. The ideal acoustic impedance of the resin layer 49 can be computed by using the same equation as the equation (1) shown above.

If a silicone-based resin is used to form the resin layer 49, the transmitting/receiving base plate 43 with the resin layer 49 can be maintained in more intimate contact with a living body because of the softness of the silicone-based resin. The air layer existing between the living body and the transmitting/receiving base plate 43 is thus made thinner, so that the attenuation of ultrasound vibration caused by the air layer can be reduced. Silicone-based resins are favorable in terms of compatibility with a living body and can be used by being maintained in intimate contact with a skin without any considerable risk of affecting the skin.

A two-resin-layer structure may also be formed in such a manner that a resin layer of an epoxy-based resin is formed on the other surface 43b of the base plate 43 and another resin layer of a silicone-based resin is formed on the epoxy resin layer, thereby limiting reflection and attenuation of ultrasound.

Figure 9:
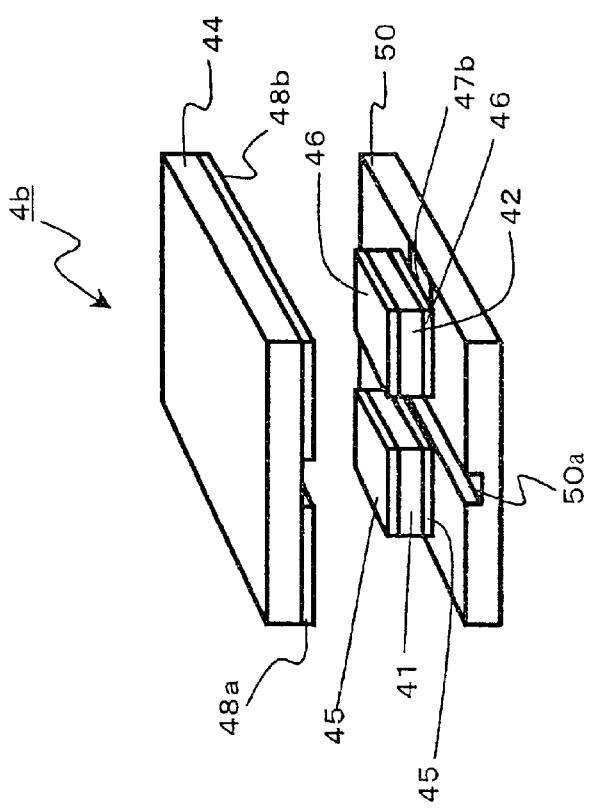
FIG. 9 is a diagram showing the structure of a measuring unit having a transmitting/receiving base plate in which a groove is formed.

FIG. 9 shows the construction of a measuring unit 4b in which the transmitting piezoelectric element 41 and the receiving piezoelectric element 42 are placed on the opposite sides of a groove 50a formed in a transmitting/receiving base plate 50.

As shown in FIG. 9, the groove 50a is formed on the transmitting/receiving base plate 50, and the transmitting piezoelectric element 41 and the receiving piezoelectric element 42 are placed on the opposite sides of the groove 50a.

Thus, ultrasound emitted from the transmitting piezoelectric element 41 at the time of detection of a pulse is reflected and attenuated by the groove 50a of the transmitting/receiving base plate 50. Therefore, the possibility of ultrasound propagating through the transmitting/receiving base plate 50 to be directly received by the receiving piezoelectric element 42 is reduced, thus reducing noise mixed in the result of measurement of a pulse. The shape of the groove 50a can be freely selected. For example, the cross-sectional configuration of the groove 50a may have a V-shape.

Figure 10:
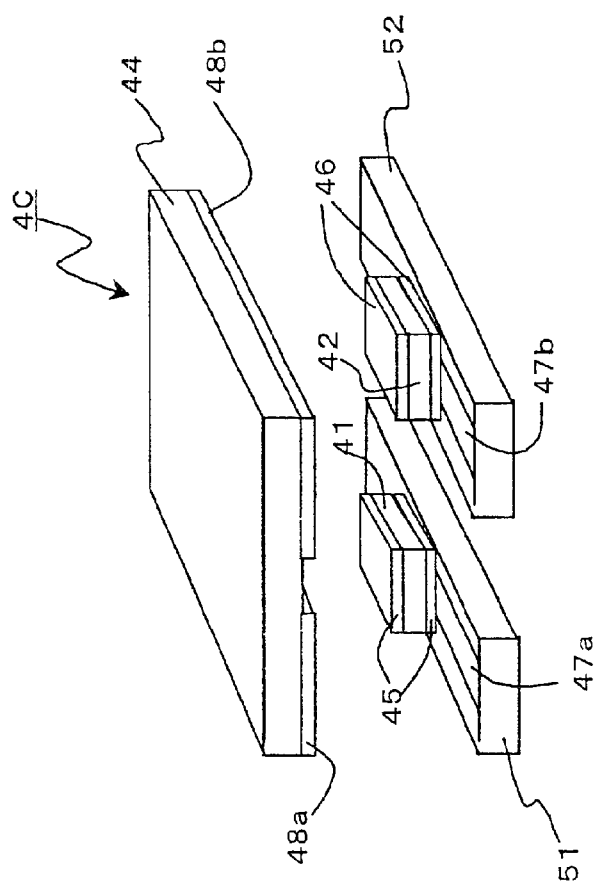
FIG. 10 is a diagram showing the structure of a measuring unit having divided transmitting/receiving base plates.

FIG. 10 shows the construction of a measuring unit 4c in which the transmitting piezoelectric element 41 and the receiving piezoelectric element 42 are placed on divided transmitting/receiving base plates 51 and 52.

As shown in FIG. 10, the measuring unit 4c has the two transmitting/receiving base plates 51 and 52 corresponding to halves of the transmitting/receiving base plate 43 (FIG. 3). The transmitting piezoelectric element 41 is placed on the transmitting/receiving base plate 51, and the receiving piezoelectric element 42 is placed on the transmitting/receiving base plate 52.

Therefore, it is not possible for ultrasound emitted from the transmitting piezoelectric element 41 at the time of detection of a pulse to propagate directly to the receiving piezoelectric element 42. Thus, occurrence of noise can be prevented during measurement of a pulse.

FIG. 11 shows the construction of a measuring unit 4d having a tapered transmitting/receiving base plate 53. As shown in FIG. 11, the transmitting/receiving base plate 53 of the measuring unit 4d has a tapered shape such that the other surface 53b to be brought into contact with a living body is slanted. The direction along which the transmitting/receiving base plate 53 is tapered corresponds to the flowing direction of a bloodstream in the living body. Thus, ultrasound emitted from the transmitting piezoelectric element 41 is obliquely transmitted to the bloodstream in the living body so that the Doppler effect of the bloodstream is enhanced, thereby improving the ultrasound receiving sensitivity of the receiving piezoelectric element 42.

FIG. 12 shows the construction of a measuring unit 4e having divided transmitting/receiving base plates 54 and 55 each having a tapered shape. As shown in FIG. 12, the measuring unit 4e has the two transmitting/receiving base plates 54 and 55 corresponding to halves of the transmitting/receiving base plate 43 (FIG. 3). The transmitting piezoelectric element 41 is placed on a surface 54a of the transmitting/receiving base plate 54, and the receiving piezoelectric element 42 is placed on the surface 55a of the transmitting/receiving base plate 55. Each of the other surface 54a of the transmitting/receiving base plate 54 and the other surface 55a of the transmitting/receiving base plate 55 is formed so as to be slanted for tapering. The direction along which each of the transmitting/receiving base plates 54 and 55 is tapered corresponds to the flowing direction of a bloodstream in a living body, and the tapered shape is such that each of the transmitting/receiving base plates 54 and 55 is larger in thickness at the outer end than at the inner end.

The transmitting/receiving base plates 54 and 55 are thus formed to enable ultrasound emitted from the transmitting piezoelectric element 41 to be suitably focused on a point about the bloodstream in the living body. Thus, the ultrasound reflected by the bloodstream in the living body can be efficiently received by the receiving piezoelectric element 42.

Figure 14:
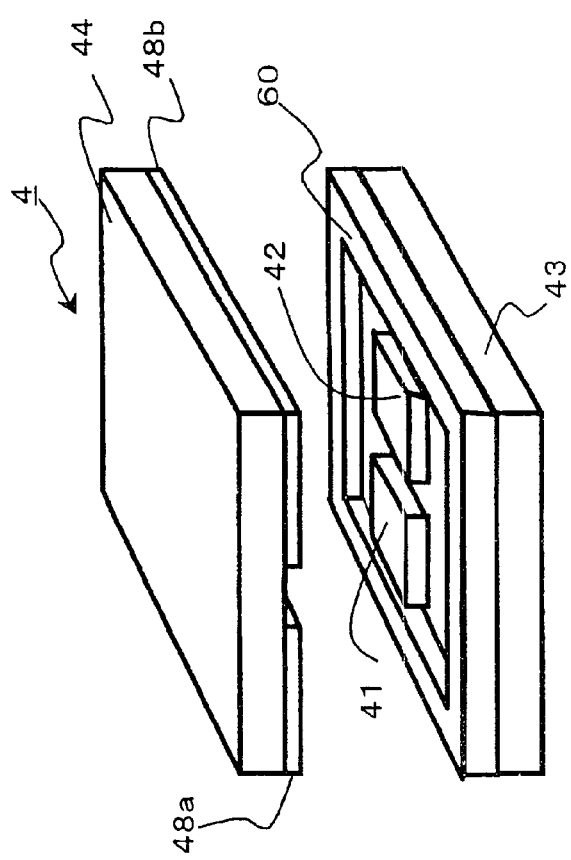
FIG. 14 is a diagram showing a structure in which a sealing material is provided between a transmitting/receiving base plate and a supporting base plate.
Figure 13:
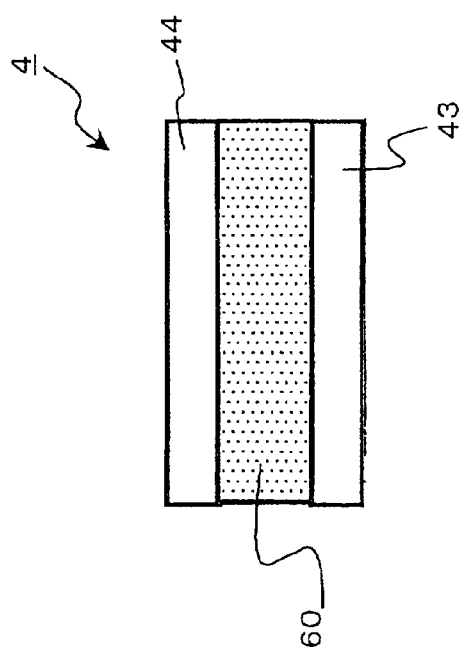
FIG. 13 is a diagram showing a structure in which a sealing material is provided between a transmitting/receiving base plate and a supporting base plate.

FIG. 13 shows a structure in which a sealing material 60 is provided between the transmitting/receiving base plate 43 and the supporting base plate 44. FIG. 14 shows a structure in which the sealing material 60 is placed so as to surround the piezoelectric elements 41 and 42. During use of the measuring unit 4 in contact with a skin, there is a possibility that sweat or the like enters the space between the transmitting/receiving base plate 43 and the supporting base plate 44. A potential difference is caused in the direction of thickness of each of the piezoelectric elements 41 and 42 through the electrodes 47a and 47b or 48a and 48b to thereby drive the piezoelectric element 41 or 42. Therefore, when sweat or the like enters the space to reaches the piezoelectric element 41 or 42, the electrodes 47a and 47b or 48a and 48b are short-circuited, resulting in failure to apply the desired potential.

Sealing material 60 is therefore provided as shown in FIG. 13 to prevent sweat or the like from entering. Silicone gel or the like is suitably used as the sealing material 60. However, silicone gel can easily transmit ultrasound. If silicone gel used as the sealing material 60 is in contact with the piezoelectric elements 41 and 42, external noise vibration propagates to the piezoelectric elements 41 and 42. Therefore, the sealing material 60 is placed so as to surround the piezoelectric elements 41 and 42, as shown in FIG. 14, thereby enabling prevention of entering of sweat or the like without causing noise.

Further, the transmitting/receiving base plate 43 and the supporting base plate 44 can be fixed by the sealing material 60, so that the durability of the measuring unit is improved.

In this embodiment, silicone gel is used as the sealing material 60. However, silicon rubber and any other kind of rubber may be used instead of silicone gel.

FIG. 15 shows a structure in which a channel 66 is formed in the transmitting/receiving base plate 43, and the transmitting piezoelectric element 41 and the receiving piezoelectric element 42 are placed in the channel 66. FIG. 16 is a side view of the structure shown in FIG. 15. When an external force is applied to a structure in which the transmitting/receiving base plate 43 and the supporting base plate 44 are connected to each other only by the piezoelectric elements 41 and 42, a stress is directly caused in the piezoelectric elements. In the structure shown in FIGS. 15 and 16, the channel 66 is formed in the transmitting/receiving base plate 43, and the piezoelectric elements 41 and 42 are placed in the channel 66. In this manner, the transmitting/receiving base plate 43 and the supporting base plate 44 are connected not only by the piezoelectric elements 41 and 42 but also by direct fixation between them. Therefore, even when an external force is applied, no considerable stress is directly caused in the piezoelectric elements 41 and 42. Consequently, this structure is not easily breakable.

If the thickness of the transmitting/receiving base plate 43 is set to about ¼ of the wavelength of ultrasound transmitted by the transmitting piezoelectric element 41, and if the frequency of the ultrasound is 9.0 MHz, the thickness of the transmitting/receiving base plate 43 is about 140 µm. If the frequency is further increased, the thickness has to be further reduced. Even in the case of using a glass base plate, the glass base plate is difficult to handle if the thickness of the base plate is thinner than about 200 µm. In the measuring unit 4 of the structure shown in FIGS. 15 and 16, the thickness H of the thinner portion of the transmitting/receiving base plate 43 remaining after forming the channel 66 is set to about ¼ of the wavelength of ultrasound transmitted by the transmitting piezoelectric element 41, thereby enabling efficient transmission and reception of ultrasound without reducing the thickness of the entire transmitting/receiving base plate 43.

Figure 17:
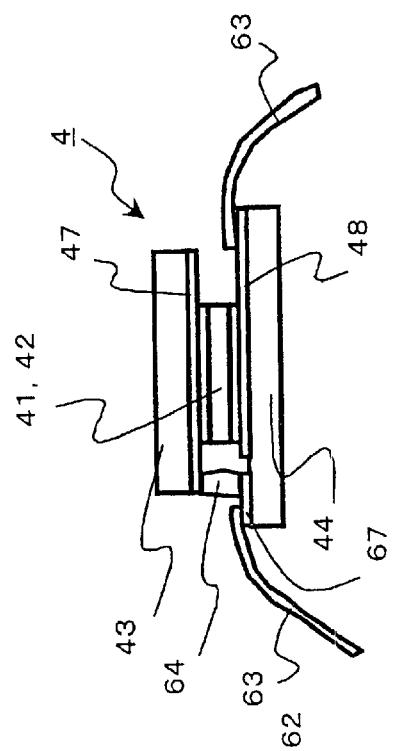
FIG. 17 is a diagram showing a structure in which a wiring member is interposed between a transmitting/receiving base plate and a supporting base plate.

FIG. 17 shows the construction of a measuring unit in which a wiring member 62 is interposed between the transmitting/receiving base plate 43 and the supporting base plate 44. The structure of the wiring member 62 is such that electrodes 61 are formed on both surfaces thereof. In this embodiment, the thickness of the piezoelectric elements 41 and 42 is set to about 0.2 mm. Thus, if a flexible printed circuit member having a thickness of about 0.2 mm is used as the wiring member 62, it can be fitted in the gap between the transmitting/receiving base plate 43 and the supporting base plate 44. The electrodes 61 are electrically connected to the electrodes 47 provided on the transmitting/receiving base plate 43 and to the electrodes 48 provided on the supporting base plate 44. Thus, different voltages can be applied between the thickness-direction-opposite surfaces of the piezoelectric element 41 and between the corresponding two surfaces of the piezoelectric element 42, respectively. Accordingly, wiring is simplified, thereby improving the facility with which the measuring unit is manufactured.

Figure 18:
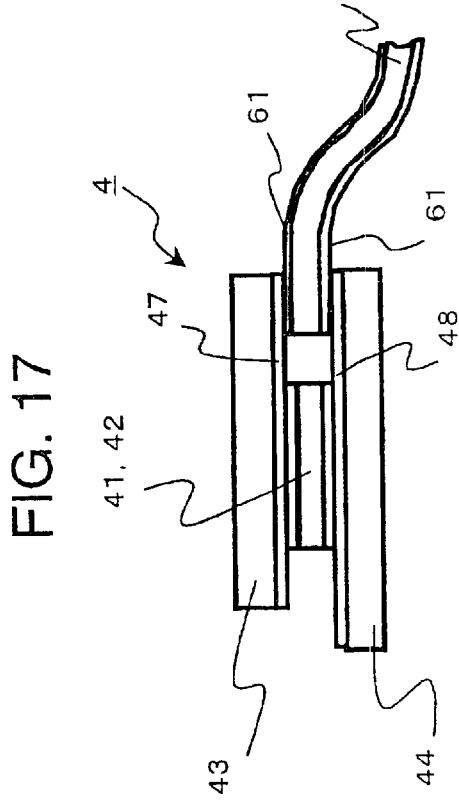
FIG. 18 is a diagram showing a structure in which electrical connections are established between a transmitting/receiving base plate and a supporting base plate.
Figure 19:
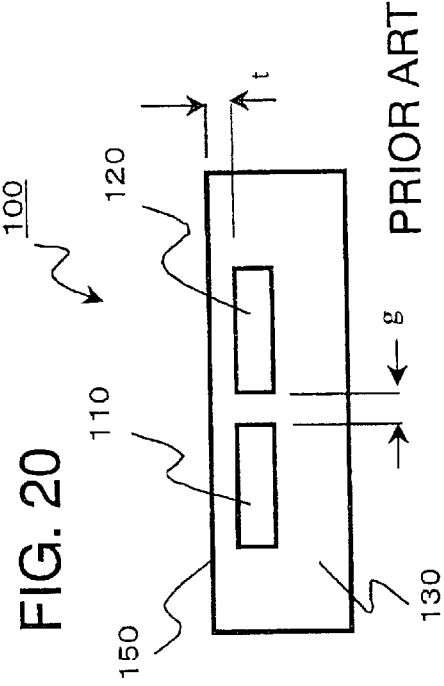
FIG. 19 is a diagram schematically showing a conventional pulse detection device using piezoelectric elements.
Figure 20:
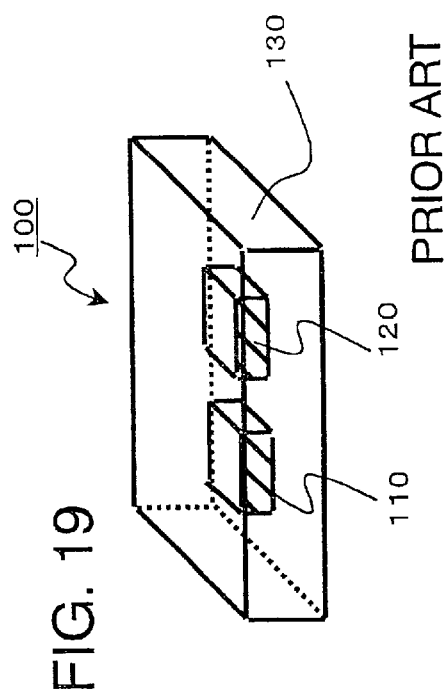
FIG. 20 is a schematic side view of the conventional pulse detection device shown in FIG. 19.

FIG. 18 shows the construction of a measuring unit in which electrodes 48 and 67 are provided on the supporting base plate 44, and the electrodes 47 provided on the transmitting/receiving base plate 43 and the electrodes 67 provided on the supporting base plate 44 are electrically connected to each other.

Ordinarily, wiring is provided for connection to each of the pair of the electrodes 47 on the transmitting/receiving base plate 43 and the pair of the electrodes 48 on the supporting base plate 44. However, the step of joining the two base plates and the piezoelectric elements 41 and 42 after providing wiring conductors on the two base plates is troublesome, and a stress is easily caused in the wiring conductors, which leads to the fragile connection structure. If wiring is provided on the transmitting/receiving substrate 43, there is a possibility of unnecessary vibration propagating through the wiring to be received by the receiving piezoelectric element, or vibration from the transmitting piezoelectric element propagating directly through the wiring.

However, if the measuring unit is constructed as shown in FIG. 18, wiring may be provided only to the side of the supporting base plate 44, whereby the measuring unit is easily manufactured. Besides, an unnecessary force cannot easily be applied to the wiring 63 and the durability of the measuring unit can be improved. Further, in this structure, noise vibration cannot propagate easily.

In this embodiment, soldering bumps 64 are provided for electrical connection between the electrodes 47 and the electrodes 67. A conductive rubber or the like may be used instead of the soldering bumps 64.

This structure may be combined with use of a sealing material such as shown in FIGS. 13 and 14 and with a channeled structure such as shown in FIGS. 15 and 16.

According to the present invention, as described above, the transmitting piezoelectric element and the receiving piezoelectric element of the pulse detection device can be placed with accuracy on the first surface of transmitting/receiving base plate in accordance with a design. It is therefore possible to provide a pulse detection device with a reduced possibility of occurrence of variation in quality. It is also possible to improve the pulse detection sensitivity of the pulse detection device.

It is possible to limit reflection of ultrasound at the interface between the transmitting/receiving base plate and the living body by controlling the acoustic impedance of the transmitting/receiving base plate or the thickness of the transmitting/receiving base plate. Thus, efficient propagation of ultrasound can be achieved, improving the pulse detection sensitivity.

The resin layer may be provided on the second surface of the transmitting/receiving base plate of the pulse detection device to optimize, according to use of the pulse detection device, the characteristics of the surface of the transmitting/receiving base plate to be brought into contact with a living body.

An epoxy-based resin may be used as the resin layer on the second surface to further reduce reflection of ultrasound at the interface between the transmitting/receiving base plate and a living body, thus enabling efficient propagation of ultrasound.

Further, a silicone-based resin may be used as the resin layer on the second surface to improve the closeness of contact between the transmitting/receiving base plate and a living body. The air layer at the interface between the transmitting/receiving base plate and the living body is thus reduced to limit attenuation of ultrasound vibration.

The groove may be formed in the transmitting/receiving base plate and the transmitting piezoelectric element and the receiving piezoelectric element may be placed on the opposite sides of the groove. In this case, ultrasound emitted from the transmitting piezoelectric element is not directly received by the receiving piezoelectric element, thereby reducing noise and improving the reliability of the pulse detection device.

The second surface of the transmitting/receiving base plate is formed so as to be slanted relative to the first surface. That is, the first and second surfaces are formed so as to be not parallel but tapered, thereby enhancing the Doppler effect of a bloodstream to improve the pulse detection sensitivity.

Further, the supporting base plate is provided to support the transmitting piezoelectric element and the receiving piezoelectric element positioned on the transmitting/receiving base plate, thereby improving the strength against an external impact and limiting leakage of ultrasound.

It is possible to grasp the result of detection of a pulse from a living body through the display section provided in the pulse detection device.

The belt for wearing the pulse detection device may be provided to facilitate carrying of the pulse detection device.

The sealing material may be provided between the transmitting/receiving base plate and the supporting base plate to prevent a reduction in sensitivity due to permeation of sweat or the like, thus improving the durability.

The channel may be formed in the transmitting/receiving base plate and the transmitting piezoelectric element and the receiving piezoelectric element may be placed in the channel, thereby reducing the possibility of occurrence of a stress in the piezoelectric elements to improve the durability.

The electrodes provided on the transmitting/receiving base plate and the electrodes provided on the supporting base plate may be electrically connected to improve the facility with which the device is manufactured and to improve the durability of the device.

The transmitting piezoelectric element and/or the receiving piezoelectric element, and the transmitting/receiving base plate may be bonded by intermetallic bonding to limit attenuation of ultrasound at the joint interface. The efficiency of propagation of ultrasound is thus improved.

What is claimed is:

1. A pulse detection device comprising:
   a base plate having a first main surface disposable against a part of a living body during use of the pulse detection device, a second main surface disposed opposite the first main surface, and a channel formed in the second main surface;
   a first piezoelectric element disposed in the channel of the base plate for transmitting an ultrasonic signal toward an artery in the living body; and
   a second piezoelectric element disposed in the channel of the base plate for receiving the ultrasonic signal transmitted by the first piezoelectric element and reflected by the artery.

2. A pulse detection device comprising:
   a base plate having a first main surface disposable against a part of a living body during use of the pulse detection device, a second main surface disposed opposite the first main surface, and a channel formed in the second main surface;
   a transmitting piezoelectric element disposed in the channel of the base plate for generating an ultrasonic signal and transmitting the ultrasonic signal toward an artery in the living body;
   a receiving piezoelectric element disposed in the channel of the base plate for receiving the ultrasonic signal transmitted by the transmitting piezoelectric element and reflected by the artery and for converting the reflected ultrasonic signal into an electrical signal; and
   a detection section for detecting a pulse from the electrical signal.

3. A pulse detection device according to claim 2; wherein the base plate has an acoustic impedance value which is intermediate an acoustic impedance value of each of the piezoelectric elements and an acoustic impedance value of the living body.

4. A pulse detection device according to claim 2; wherein the base plate comprises a glass base plate having a thickness of about ¼ of a wavelength of the ultrasonic signal generated by the transmitting piezoelectric element.

5. A pulse detection device according to claim 2; further comprising a resin layer disposed on the first main surface of the base plate.

6. A pulse detection device according to claim 5; wherein the resin layer comprises an epoxy-based resin.

7. A pulse detection device according to claim 5; wherein the resin layer comprises a silicone-based resin.

8. A pulse detection device according to claim 2; further comprising a support plate for supporting the transmitting piezoelectric element and the receiving piezoelectric element disposed in the channel of the base plate.

9. A pulse detection device according to claim 8; further comprising a sealing material disposed between the base plate and the support plate.

10. A pulse detection device according to claim 9; wherein the sealing material surrounds the transmitting and receiving piezoelectric elements without contacting the transmitting and receiving piezoelectric elements.

11. A pulse detection device according to claim 2; wherein a thickness of a portion of the base plate from a base of the channel to the first main surface thereof is about ¼ of a wavelength of the ultrasonic signal generated by the transmitting piezoelectric element.

12. A pulse detection device according to claim 8; further comprising at least one first electrode disposed on the second main surface of the base plate and at least one second electrode electrically connected to the first electrode and disposed on a surface of the support plate.

13. A pulse detection device according to claim 8; further comprising a metallic bonding for connecting at least one of the transmitting piezoelectric element and the receiving piezoelectric element to the base plate.

14. A pulse detection device according to claim 2; further comprising an electrode disposed on the second main surface of the base plate for applying a voltage to the transmitting and receiving piezoelectric elements.

15. A pulse detection device according to claim 8; further comprising a flexible printed circuit board disposed between the base plate and the support plate and having an electrode for applying a voltage to the transmitting and receiving piezoelectric elements.

16. A pulse detection device according to claim 9; wherein the sealing material comprises silicone resin.

17. A pulse detection device comprising: a base plate having a first surface disposable against a part of a living body and a second surface disposed opposite the first surface; a resin layer disposed on the first surface of the base plate; a transmitter provided on the base plate so as to not protrude from the second surface of the base plate for transmitting an ultrasonic signal toward an artery in the living body; a receiver provided on the base plate so as to not protrude from the second surface of the base plate for receiving the ultrasonic signal transmitted by the transmitter and reflected by the artery; a support plate for supporting the transmitter and the receiver; and a sealing material disposed between the base plate and the support plate and surrounding the transmitter and the receiver without contacting the transmitter and the receiver.

18. A pulse detection device comprising: a base plate having a first surface disposable against a part of a living body and a second surface disposed opposite the first surface; a resin layer disposed on the first surface of the base plate; a transmitter provided on the base plate so as to not protrude from the second surface of the base plate for transmitting an ultrasonic signal toward an artery in the living body; a receiver provided on the base plate so as to not protrude from the second surface of the base plate for receiving the ultrasonic signal transmitted by the transmitter and reflected by the artery; a support plate for supporting the transmitter and the receiver; and a flexible printed circuit board disposed between the base plate and the support plate and having an electrode for applying a voltage to the transmitter and the receiver.

19. A pulse detection device comprising: a base plate having a first surface disposable against a part of a living body and a second surface disposed opposite the first surface; a transmitter provided on the base plate so as to not protrude from the second surface of the base plate for transmitting an ultrasonic signal toward an artery in the living body; a receiver provided on the base plate so as to not protrude from the second surface of the base plate for receiving the ultrasonic signal transmitted by the transmitter and reflected by the artery; and a channel formed in the second surface of the base plate, the transmitter and the receiver being disposed in the channel so as to not protrude from the second surface of the base plate.

20. A pulse detection device comprising:

transmitting means for transmitting an ultrasonic wave toward an artery;

receiving means for receiving the ultrasonic wave transmitted by the transmitting means and reflected by the artery;

a base plate having a first surface disposable against a part of a living body containing the artery and a second surface disposed opposite the first surface, the transmitting means and the receiving means being disposed on the base plate so as to not protrude from the second surface; and a channel formed in the second surface of the base plate, the transmitting means and the receiving means being disposed in the channel so as to not protrude from the second surface of the base plate.

21. A pulse detection device according to claim 20; further comprising pulse information acquiring means for acquiring an ultrasonic wave signal from the receiving means and determining pulse information based on the ultrasonic wave signal; and output means for outputting the pulse information from the pulse information acquiring means.

* * * * *